(12) United States Patent
Janssen

(10) Patent No.: US 7,175,895 B2
(45) Date of Patent: *Feb. 13, 2007

(54) GLOVE WITH MEDICATED POROUS BEADS

(75) Inventor: Robert Allen Janssen, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 221 days.

This patent is subject to a terminal disclaimer.

(21) Appl. No.: 10/716,767

(22) Filed: Nov. 19, 2003

(65) Prior Publication Data

US 2005/0106201 A1  May 19, 2005

(51) Int. Cl.
*B32B 27/08* (2006.01)
*B32B 5/16* (2006.01)
*A41D 19/00* (2006.01)
*A41D 19/015* (2006.01)
*A41D 13/08* (2006.01)
*A01N 25/34* (2006.01)
*B29D 22/00* (2006.01)

(52) U.S. Cl. .................. 428/35.7; 428/36.8; 428/143; 428/144; 428/147; 428/323; 428/327; 428/338; 428/339; 2/161.7; 2/168; 424/402

(58) Field of Classification Search ............ 428/35.7, 428/36.8, 143, 144, 147, 323, 327, 338, 339; 2/161.7, 168; 424/402
See application file for complete search history.

(56) References Cited

U.S. PATENT DOCUMENTS

| | | | |
|---|---|---|---|
| 4,070,713 A | 1/1978 | Stockum | 2/168 |
| 4,143,109 A | 3/1979 | Stockum | 264/112 |
| 4,675,347 A | 6/1987 | Mochizuki et al. | 523/122 |
| 4,810,543 A | 3/1989 | Gould et al. | 428/35.7 |
| 4,853,978 A | 8/1989 | Stockum | 2/167 |
| 5,019,096 A | 5/1991 | Fox, Jr. et al. | 623/1 |
| 5,071,648 A | 12/1991 | Rosenblatt | 424/78.06 |
| 5,073,365 A | 12/1991 | Katz et al. | 424/489 |
| 5,133,090 A | 7/1992 | Modak et al. | 2/168 |
| 5,138,719 A | 8/1992 | Orlianges et al. | 2/168 |
| 5,236,703 A | 8/1993 | Usala | 424/78.36 |
| 5,492,692 A | 2/1996 | Digenis et al. | 424/78.25 |
| 5,549,924 A | 8/1996 | Shlenker et al. | 427/2.3 |
| 5,616,338 A | 4/1997 | Fox, Jr. et al. | 424/423 |
| 5,674,513 A | 10/1997 | Snyder, Jr. et al. | 424/404 |
| 5,679,399 A | 10/1997 | Shlenker et al. | 427/2.3 |
| 5,742,943 A | 4/1998 | Chen | 2/168 |
| 5,922,336 A | 7/1999 | Tebbe | 424/402 |
| 5,965,276 A | 10/1999 | Shlenker et al. | 428/492 |
| 5,968,538 A | 10/1999 | Snyder, Jr. | 424/404 |
| 5,993,923 A | 11/1999 | Lee | 428/36.8 |

(Continued)

FOREIGN PATENT DOCUMENTS

EP  0105613  4/1984

(Continued)

*Primary Examiner*—Jennifer C. McNeil
*Assistant Examiner*—Chris Bruenjes
(74) *Attorney, Agent, or Firm*—Vincent T. Kung; Scott B. Garrison

(57) ABSTRACT

An elastomeric article includes a substrate body formed from an elastomeric material, and a plurality of porous beads capable of containing a treatment within the pores of the beads and dispensing the treatment to an end user.

20 Claims, 2 Drawing Sheets

U.S. PATENT DOCUMENTS

| | | | |
|---|---|---|---|
| 5,993,972 A | 11/1999 | Reich et al. | 428/423.1 |
| 6,051,320 A | 4/2000 | Noecker et al. | 428/447 |
| 6,074,671 A | 6/2000 | Oldham et al. | 424/486 |
| 6,120,784 A | 9/2000 | Snyder, Jr. | 424/404 |
| 6,306,514 B1 | 10/2001 | Weikel et al. | 428/451 |
| 6,420,455 B1 | 7/2002 | Landgrebe et al. | 523/122 |
| 6,638,587 B1 | 10/2003 | Wang et al. | 428/35.7 |
| 6,641,879 B1 * | 11/2003 | Matsuura et al. | 428/35.7 |
| 6,972,148 B2 * | 12/2005 | Janssen | 428/147 |

FOREIGN PATENT DOCUMENTS

| | | |
|---|---|---|
| EP | 0371850 | 6/1990 |
| EP | 0328421 B1 | 4/1993 |
| EP | 0543657 | 5/1993 |
| EP | 0678036 B1 | 4/1997 |
| EP | 0865778 | 9/1998 |
| EP | 1360940 | 11/2003 |
| WO | WO 96/23428 | 8/1996 |
| WO | WO 00/09320 | 2/2000 |
| WO | WO 03/22962 | 3/2003 |
| WO | WO 03/102058 | 12/2003 |
| WO | WO 2004/060432 | 7/2004 |

\* cited by examiner

US 7,175,895 B2

GLOVE WITH MEDICATED POROUS BEADS

BACKGROUND OF THE INVENTION

Tightly fitting elastomeric articles, such as surgical and examination gloves, may be difficult to don due to blocking, the tendency of the glove to stick to itself. As a result, gloves often contain a powdered lubricant on the surface that contacts the skin of the wearer to facilitate donning. Most commonly, epichlorohydrin treated crosslinked cornstarch is dusted on the inner surface of the glove during manufacturing.

While use of cornstarch does improve the donning characteristics of the glove, it may not be feasible for all applications. One such situation is the use of powders for surgical glove applications. If some of the powder inadvertently enters the surgical site, it may cause complications for the patient. For instance, the powder may carry an infectious agent or the patient may be allergic to the powder.

Other techniques may be used to improve the donning characteristics of surgical and examination gloves. These techniques include, for example, manufacturing the glove from a modified latex, using an inner layer of a hydrophilic polymer, applying a slip coating to the inner surface of the glove, and the like. However, as some degree of blocking may still occur with these techniques, there remains a need for a glove with improved donning characteristics.

SUMMARY OF THE INVENTION

The present invention generally relates to an elastomeric article, for example, a glove. The article includes a substrate body formed from an elastomeric material, and a plurality of porous beads covalently bonded to the elastomeric material. The porous beads have pore sizes ranging from about 0.01 microns to about 0.5 microns. Within the pores is a treatment that is releasable to the environment. The porous beads may generally be formed from a polymer having a vinyl group. The vinyl group may be a carbon-carbon vinyl group or an acrylate group. In some embodiments, the environment is the skin of an end-user. The treatment may consist of a moisturizer, an ointment, a drug, and an emollient. In some instances, the article may include from about 0.0001 mass % to about 10 mass % porous beads. In other instances, the article may include from about 0.001 mass % to about 5 mass % porous beads. In yet other instances, the article may include from about 0.01 mass % to about 3 mass % porous beads.

The present invention also relates to an elastomeric article including a substrate body having a first surface, and a donning layer overlying the first surface, where the donning layer includes a polymeric material and a plurality of covalently bonded porous beads. In some instances, the polymeric material may include a hydrogel. The porous beads have pore sizes ranging from about 0.01 microns to about 0.5 microns. Within the pores is a treatment that is releasable to the environment. In some instances, the donning layer may include from about 0.01 mass % to about 80 mass % porous beads. In other instances, the donning layer may include from about 1 mass % to about 50 mass % porous beads. In yet other instances, the donning layer may include from about 10 mass % to about 25 mass % porous beads.

DESCRIPTION OF THE INVENTION

The present invention generally relates to an elastomeric article having improved donning characteristics, for example a condom or glove. As used herein, the term "elastomeric article" refers to an article formed predominantly from an elastomeric material. The article includes a plurality of porous beads on the wearer-contacting surface of the article to facilitate donning and to contain and dispense a treatment. The beads are covalently bonded to the material that forms the article, so no separate binder material is needed to affix the beads to the article. The beads cause the overall surface area of the wearer-contacting surface to be reduced, thereby facilitating donning. The beads are also capable of containing and dispensing, over time, a treatment that may provide a desirable benefit to an end user. To better understand the present invention, a more detailed description is provided below.

Figure 1:
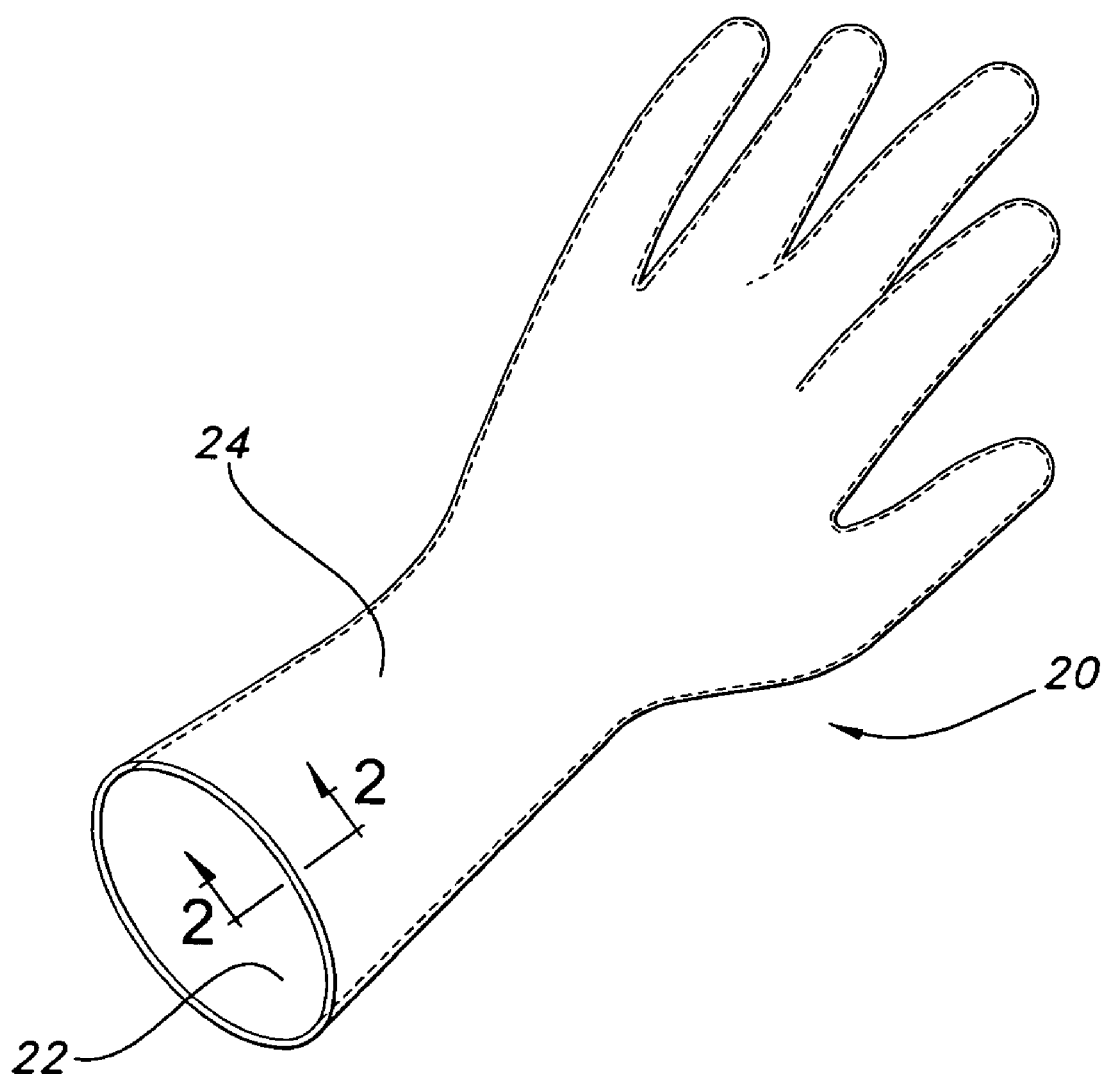
FIG. 1 depicts an article that may be formed according to the present invention, namely a glove.

An elastomeric article to be formed, for example, a glove 20 (FIG. 1) includes an inside, or wearer-contacting, surface 22 and an outside surface 24. The inside surface 22 has a textured topography due to the presence of a plurality of porous beads 34 (best seen in FIGS. 2A and 2B) covalently bonded to the material that forms the inside surface 22. As used herein, the term "inside surface" refers to the surface of the article that contacts the body of the wearer. As used herein, the term "outside surface" refers to the surface of the article that is distal from the body of the wearer. The beads do not extend through the entire thickness of the glove, so the barrier properties of the glove are not compromised.

Figure 2A:
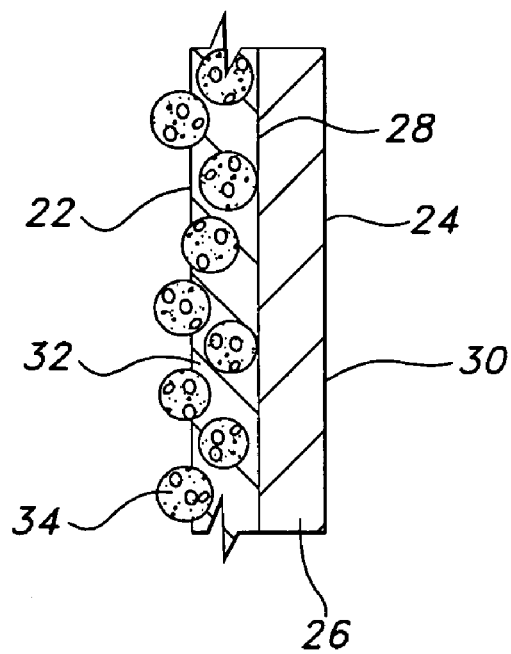
FIG. 2A depicts a schematic cross-sectional illustration of the article of FIG. 1 taken along a line 2—2, the article including a substrate body and a donning layer, where the donning layer includes a plurality of covalently bonded porous beads.
Figure 2B:
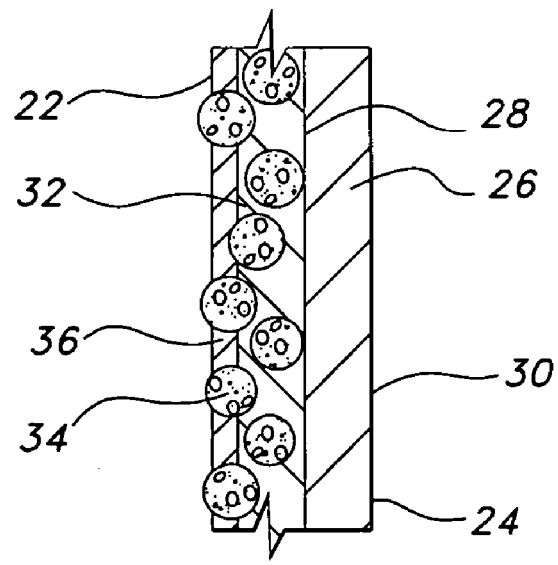
FIG. 2B depicts another schematic cross-sectional illustration of the article of FIG. 1 taken along a line 2—2, the article including a substrate body, a donning layer, and a lubricant layer, where the donning layer includes a plurality of covalently bonded porous beads.

The glove includes a substrate body 26 having a first surface 28 and a second surface 30 (FIG. 2A–2B). As used herein, "first surface" refers to the surface of the substrate body proximal to the body of the wearer. As used herein, "second surface" refers to the surface of the substrate body distal to the body of the wearer.

The article of the present invention may include a single layer or multiple layers as desired. In a single layer glove including only the substrate body, the first surface may form the inside surface of the glove. However, in a multi-layer glove having additional layers proximal to the body of the wearer, the additional layer or layers may each form a portion of the inside surface, or the entire inside surface, as desired. Likewise, in a single layer glove including only the substrate body, the second surface may form the outside surface of the glove. However, in a multi-layer glove having additional layers distal from the body of the wearer, the additional layer or layers may each form a portion of the outside surface, or the entire outside surface, as desired.

For example, as depicted in FIG. 2A, the article may include a donning layer 32 overlying at least a portion of the first surface 28 of the substrate body 26. In such an article, the donning layer 32 forms at least a portion of the inside surface 22 of the glove 20. In some such embodiments, the donning layer may include a plurality of porous beads 34 covalently bonded to the material that forms the donning layer. As depicted in FIG. 2B, the article may also include other layers, such as a lubricant layer 36 that overlies at least a portion of the donning layer 32. In such an article, the lubricant layer 36 forms at least a portion of the inside surface 22 of the glove 20.

The article of the present invention may be formed from any suitable elastomeric material, and by any suitable technique, for example dipping, spraying, tumbling, drying, and curing. As used herein, the term "elastomeric material" refers to a polymeric material that is capable of being easily stretched or expanded, and will substantially return to its previous shape upon release of the stretching or expanding force. In one embodiment, the elastomeric material may include natural rubber, which is generally provided as a natural rubber latex. In another embodiment, the elastomeric material may include nitrile butadiene rubber, and in particular, may include carboxylated nitrile butadiene rubber. In other embodiments, the elastomeric material may include a styrene-ethylene-butylene-styrene block copolymer, styrene-isoprene-styrene block copolymer, styrene-butadiene-styrene block copolymer, styrene-isoprene block copolymer, styrene-butadiene block copolymer, synthetic isoprene, chloroprene rubber, polyvinyl chloride, silicone rubber, or a combination thereof.

The article of the present invention, for example, the glove 20, may include a donning layer 32 overlying at least a portion of the first surface 28 of the substrate body 26 (FIG. 2A). The donning layer may be formed from any polymeric material that is capable of facilitating donning of the glove. Some examples of suitable materials for the donning layer 28 include, but are not limited to, polybutadienes, for example, 1,2-syndiotactic polybutadiene, polyurethanes, acrylic polymers, and the like.

In one embodiment, the polymeric material that forms the donning layer may include a hydrogel. As used herein, the term "hydrogel" refers to a polymeric material that is capable of absorbing more than 20% its weight in water while maintaining a distinct three-dimensional structure. A hydrogel may be formed from a variety of hydrophilic monomers. Examples of monomers that may be used to form a hydrogel that may be suitable for use with the present invention include hydroxy ethyl methacrylate (HEMA), hydroxy ethyl acrylate (HEA), methacrylic acid (MAA), acrylic acid (AA), vinyl pyrrolidone, acrylamide, dimethyl acrylamide, and so forth. While several hydrophilic monomers are set forth herein, it should be understood that any hydrophilic monomer may be polymerized to form a hydrogel that may be suitable for use with the present invention.

In some instances, it may be desirable to copolymerize a hydrophobic monomer with a hydrophilic monomer. By doing so, the mechanical properties and the performance characteristics of the resulting hydrogel may be modified for a particular application. Examples of such hydrophilic monomers include 2-ethyl hexyl acrylate (EHA), methyl methacrylate, styrene, butyl acrylate, hydroxy propyl methacrylate, and acrylated silicone oligomers. While several hydrophobic monomers are set forth herein, it should be understood that any hydrophobic monomer may be copolymerized with a hydrophilic monomer to form a hydrogel that may be suitable for use with the present invention.

Furthermore, more than two monomers may be used to form a hydrogel for use with the present invention. For instance, a hydrogel may include various ratios of HEMA, MAA, and EHA. Any ratio may be suitable for a given application, and in one embodiment, the ratio of HEMA:MAA:EHA may be about 5:1:1. Where more hydrophobic character is desired in the hydrogel, the concentration of the EHA may be increased. Thus, the properties of the hydrogel may be modified for a given application.

In another embodiment, the polymeric material that forms the donning layer may include an unsaturated styrene-isoprene-styrene (SIS) block copolymer having tri- or radial-blocks. In one such embodiment, the SIS block copolymer may have a polystyrene end block content of from about 10 mass % to about 20 mass % of the total weight of the SIS block copolymer. In another such embodiment, the SIS block copolymer may have a polystyrene end block content of from about 15 mass % to about 18 mass % of the total weight of the SIS block copolymer. Moreover, the molecular weight of the polystyrene end blocks may typically be at least about 5,000 grams per mole. Some examples of suitable mid-block unsaturated SIS block copolymers include, but are not limited to, Kraton® D1107 available from Kraton Polymers and Vector® 511 and Vector® 4111 available from Dexco Polymers of Houston, Tex.

In yet another embodiment, the polymeric material that forms the donning layer may include an unsaturated styrene-butylene-styrene (SBS) block copolymer. One example of an SBS block copolymer that may be suitable for use as a donning layer is commercially available from Dexco Polymers (Houston, Tex.) under the trade name VECTOR® 8508. VECTOR® 8508 is believed to be a linear, pure triblock copolymer (containing less than 1% diblock copolymer) produced using anionic polymerization. Another example of an SBS polymer that may be suitable for use as a donning layer is also commercially available from Dexco Polymers (Houston, Tex.) under the trade name VECTOR® 8550.

While various polymeric materials that may be used to form the donning layer are set forth herein, it should be understood that any suitable polymeric material may be used as desired.

In accordance with the present invention, the substrate body or the donning layer may include a plurality of porous beads. The beads may have any shape, and in some instances, may have a spherical shape. In other instances, the beads may have an elliptical shape. In yet other instances, the beads may have an irregular shape.

The porous beads may be formed from any material that is capable of being covalently bonded to the material that forms the substrate body or the donning layer, provided that the bead does not plasticize, dissolve, dissociate, or otherwise degrade during formation of the article.

In general, the beads may be formed from any polymer having a vinyl group. The vinyl group may then be used to covalently bond the bead to the material that forms the substrate body or the donning layer, as desired. In some embodiments, the material may include a carbon-carbon vinyl group. In other embodiments, the material may include an acrylate group.

The beads of the present invention may be formed in a variety of ways. While various techniques are described herein, it should be understood that any other suitable technique may be used.

In one embodiment, the beads may be synthesized to contain the needed vinyl functionality. Where this technique is used, the vinyl functionality will likely be present throughout the porous bead. Such materials may include polymers, copolymers, terpolymers, and so forth, of monomers having a vinyl group, for example, hydroxy ethyl methacrylate (HEMA), hydroxy ethyl acrylate (HEA), methacrylic acid (MAA), acrylic acid (AA), vinyl pyrrolidone, acrylamide, dimethyl acrylamide, 2-ethyl hexyl acrylate (EHA), methyl methacrylate, styrene, butyl acrylate, hydroxy propyl methacrylate, and acrylated silicone oligomers, and so forth. While several such monomers are set forth herein, it should be understood that any polymeric bead having a vinyl functional group may be used with the present invention.

In another embodiment, the beads may be formed from a material having a hydroxyl functionality. The beads may then be reacted with a material having the needed vinyl group to introduce the vinyl group into the material that forms the bead. Examples of materials that include hydroxyl functionality include polyvinyl alcohol, silica, and copolymers of a monomer with vinyl functionality (e.g., vinyl alcohol) and another monomer (e.g., styrene, methyl methacrylate (MMA), ethylene, or propylene).

In yet another embodiment, the beads may be formed from a material that does not have hydroxyl functionality, but that is capable of being subject to a surface conversion to produce hydroxyl groups on the surface of the bead. Examples of such materials include polymethyl methacrylate (PMMA), polyethylene, polypropylene, melamine resin, carboxylated melamine resin, polyvinyltoluene, polystyrene, copolymers of styrene and butadiene, copolymers of styrene and vinyltoluene, copolymers of styrene and divinylbenzene, and copolymers of styrene and methacrylic acid. Such beads may then be subjected to a surface conversion process by which a hydroxyl group is introduced into the starting material. For example, PMMA may be subjected to a transesterification process to introduce a hydroxyl group. Other materials, such as polypropylene and polyethylene, may be, for example, exposed to ozone followed by heating to introduce the needed hydroxyl functionality. While exemplary oxidative techniques are set forth herein, it should be understood by those skilled in the art that other oxidative techniques may be employed as desired. The hydroxyl group may then be subsequently converted to an acrylate group by reacting it with an appropriate chemistry.

Thus, in one instance, the starting material may include a plurality of PMMA beads, which do not contain the needed vinyl functionality for later covalent attachment to the substrate body or the donning layer. The PMMA beads may be suspended in aqueous ethylene glycol. Using acidic or basic conditions to catalyze a transesterification reaction, the methyl group of the PMMA are replaced with hydroxyl groups. The hydroxyl groups are then available for reaction with, for example, 2-isocyanatoethyl methacrylate. The isocyanate portion of the 2-isocyanatoethyl methacrylate reacts with the hydroxyl-modified PMMA beads to result in a surface acrylated functional bead. In another instance, the hydroxyl groups may be reacted with glycidyl methacrylate. In this instance, the epoxy portion of the glycidyl methacrylate reacts with hydroxyl-modified PMMA beads to also result in a surface acrylated functional bead.

A number of techniques may be suitable to impart the necessary porosity to the beads. For example, one synthesis technique provides that during the emulsion polymerization of the monomers used to make a bead, another polymer is added to the solution. This added polymer would be physically trapped in the matrix of the bead, but not chemically attached to the bead. Once the beads have been polymerized with the entrapped polymer, it would then be possible to extract the added polymer using a solvent within which the added polymer is soluble. Upon extraction of the soluble polymer, one is left with a bead exhibiting a controllable and desirable degree of porosity.

Another suitable method for creating porous beads is through the addition of supercritical carbon dioxide. In this case, the monomers would be dissolved in the supercritical carbon dioxide fluid. Polymerization of the beads would then be allowed to occur. However, at the end of the synthesis process, the supercritical carbon dioxide would be released to atmospheric pressure. Upon doing so, the supercritical carbon dioxide would expand and generate the desired degree of porosity in the synthesized beads.

In some embodiments, the porosity of the beads could be made to range from about 0.01 microns in diameter up to about 0.5 microns. The beads may then be impregnated with a desirable treatment or drug capable of, for example, enhancing the skin health of the user. Typical examples of such treatments include, but are not limited to moisturizers, ointments, drugs, and emollients. Some specific examples of these include but are not limited to aloe, vitamin E, lanolin, polyethylene glycol, glycerin, and mineral oil.

These treatments could be incorporated into the pores prior to the time the beads are applied to the glove or in a post operation where the pores are filled by dipping, coating, or immersing the glove in a treatment or respective drug solution. If the latter, the application of the treatment would then be followed by a rinse, such as a water rinse to remove excess drug from the surface of the glove. It is desirable to have the treatment be contained substantially within the pores of the beads alone. It is understood, however, that some quantity of the treatment may manifest itself upon the surface of the bead, but the intent is to have the treatment wholly contained within the pores themselves.

The quantity of treatment that may be incorporated into the porous beads is a function of the total void volume, i.e., the porosity of the bead with respect to the total bead. That is, if the pores result in a bead containing a 40 percent void volume, the remaining 60 percent would comprise a solid bead, and the 40 percent void volume is available for containing the respective treatment. In some embodiments, it may be desirable to provide void volumes ranging from about 0.1 percent to about 90 percent of the total volume of an exemplary bead. In other embodiments, it may be desirable to provide void volumes ranging from about 20 percent to about 50 percent of the total volume of an exemplary bead.

The rate at which the drug is released from the beads is typically a function of the diffusion rate of the treatment through the pores. Additionally, the void volume of the bead, the shear forces placed on the beads as the article is donned or otherwise exposed to play into the diffusion rate to a lesser extent. The rate of release may be defined by grams of treatment released from the bead per unit surface area of the bead over a unit of time. Therefore the rate of release can be expected to increase as the void volume of the pores in the bead increases and the rate of release will also increase dependent upon the shear rate to which the bead is subjected.

There are two basic mechanisms for the controlled timed release of the treatment to the user. The first one is by diffusion of the treatment from the pores in the beads onto the user's hands. This is due to the concentration gradient between the treatment contained within the pores as compared to the target point, for example, in the case of a glove, the user's hands. The treatment would be at 100% concentration in the pores, whereas the target, i.e., the end user's hands, would have a 0% concentration. In other words, the end user would have no treatment on his hands prior to donning the glove. This concentration gradient of 100% to 0%, causes the treatment to diffuse out of the pores and come into contact with the hands. The other mechanism causing the release of the treatment is due to the friction of the hand rubbing across the surface of the porous beads. This would result in a "dragging" shear force on the treatment at the surface of the pores and cause it to flow out onto the user's hands.

For long procedures it would be advantageous to slow down the rate at which a treatment is released from the pores. This will cause it to last longer and be more effectively utilized by the end user. On the opposite side, for short procedures, such as medical examinations, it may be advantageous to have as much of the treatment come out before the procedure is completed. This could potentially result in full utilization of the treatment contained within the beads. One way to speed up the treatment release rate would be to add a surfactant or surfactants to the treatment formulation to enhance the ability of the treatment to "wet out" onto the end user's hand. By allowing the treatment to wet out from moisture generated by the end user, it stands to reason that this will increase the rate at which the treatment flows out of the pores in the beads.

Overall, the diffusion rate may be caused to range from a near instantaneous release of the treatment from the surface of the pores to a timed release occurring over several hours. As stated above, a near instantaneous release may be produced by a "dragging" shear force.

Application of the beads to the article is accomplished as explained above. The porous beads are covalently bonded to the material that forms the substrate body. Where a donning layer is included in the article of the present invention, it may be desirable to covalently bond the beads 34 to the material that forms the donning layer 32 itself (FIG. 2A). As stated above, the porous beads may be formed in a variety of manners, including direct synthesis of the porous beads and surface conversion of polymeric beads (transesterification coupled with reaction with an appropriate chemistry to attach an acrylate group to the surface). In one instance, the porous bead may be covalently bonded to a hydrogel donning layer, which may, for example, be formed from HEMA and other monomers described above. To do so, the porous beads may be suspended in, for example, an aqueous solution of the monomers used to form the hydrogel donning layer and a free radical initiator. When free radical polymerization is initiated, the monomers form polymer chains that grow in length and also incorporate the porous beads into the structure via the acrylate functionality of the beads. Thus, the beads are covalently bonded to the hydrogel polymeric material used to form the donning layer of the glove. Additionally, as stated, the treatment may be incorporated into the beads either before or after the beads are bonded to the article.

The beads may be present in any suitable amount that facilitates donning without compromising the physical integrity of the donning layer or impeding its purpose. In some embodiments, the beads may be present in an amount of about 0.01 mass % to about 80 mass % of the resulting (dried) donning layer. In other embodiments, the beads may be present in an amount of about 1 mass % to about 50 mass % of the resulting (dried) donning layer. In yet other embodiments, the beads may be present in an amount of about 10 mass % to about 25 mass % of the resulting (dried) donning layer.

In some instances, the resulting (dried) donning layer may be present in an amount of about 5 mass % of the resulting (solidified) glove. Thus, in one embodiment, the porous beads may be present in an amount of from about 0.0001 mass % to about 10 mass % of the resulting (solidified) glove. In another embodiment, the porous beads may be present in an amount of from about 0.001 mass % to about 5 mass % of the resulting (solidified) glove. In yet another embodiment, the porous beads may be present in an amount of from about 0.01 mass % to about 3 mass % of the resulting (solidified) glove.

In some embodiments, a lubricant layer 36 (FIG. 2B) may also overlie at least a portion of the donning layer 32 to aid in donning the article. In one embodiment, the lubricant layer may include a silicone or silicone-based component. As used herein, the term "silicone" generally refers to a broad family of synthetic polymers that have a repeating silicon-oxygen backbone, including, but not limited to, polydimethylsiloxane and polysiloxanes having hydrogen-bonding functional groups selected from the group consisting of amino, carboxyl, hydroxyl, ether, polyether, aldehyde, ketone, amide, ester, and thiol groups. In some embodiments, polydimethylsiloxane and/or modified polysiloxanes may be used as the silicone component in accordance with the present invention. Some suitable modified polysiloxanes that may be used in the present invention include, but are not limited to, phenyl-modified polysiloxanes, vinyl-modified polysiloxanes, methyl-modified polysiloxanes, fluoro-modified polysiloxanes, alkyl-modified polysiloxanes, alkoxy-modified polysiloxanes, amino-modified polysiloxanes, and combinations thereof.

Examples of some suitable phenyl-modified polysiloxanes include, but are not limited to, dimethyldiphenylpolysiloxane copolymers, dimethyl and methylphenylpolysiloxane copolymers, polymethylphenylsiloxane, and methylphenyl and dimethylsiloxane copolymers. Phenyl modified polysiloxanes that have a relatively low phenyl content (less than about 50 mole %) may be particularly effective in the present invention. For example, the phenyl-modified polysiloxane may be a diphenyl-modified silicone, such as a diphenylsiloxane-modified dimethylpolysiloxane. In some embodiments, the phenyl-modified polysiloxane contains phenyl units in an amount from about 0.5 mole % to about 50 mole %. In other embodiments, the phenyl-modified polysiloxane contains phenyl units in an amount less than about 25 mole %. In yet other embodiments, the phenyl-modified polysiloxane contains phenyl units in an amount less than about 15 mole %. In one particular embodiment, a diphenylsiloxane-modified dimethylpolysiloxane may be used that contains diphenylsiloxane units in an amount less than about 5 mole %. In still another embodiment, a diphenylsiloxane-modified dimethylpolysiloxane may be used that contains diphenylsiloxane units in an amount less than about 2 mole %. The diphenylsiloxane-modified dimethylpolysiloxane may be synthesized by reacting diphenylsiloxane with dimethylsiloxane.

As indicated above, fluoro-modified polysiloxanes may also be used with the present invention. For instance, one suitable fluoro-modified polysiloxane that may be used is a trifluoropropyl modified polysiloxane, such as a trifluoropropylsiloxane modified dimethyl-polysiloxane. A trifluoropropylsiloxane modified dimethylpolysiloxane may be synthesized by reacting methyl, 3,3,3 trifluoropropylsiloxane with dimethylsiloxane. The fluoro-modified silicones may contain from about 5 mole % to about 95 mole % of fluoro groups, such as trifluoropropylsiloxane units. In another embodiment, the fluoro-modified silicones may contain from about 40 mole % to about 60 mole % of fluoro groups. In yet another embodiment, a trifluoropropylsiloxane-modified dimethylpolysiloxane may be used that contains 50 mole % trifluoropropylsiloxane units.

Other modified polysiloxanes may be utilized with the present invention. For instance, some suitable vinyl-modified polysiloxanes include, but are not limited to, vinyldimethyl terminated polydimethyl-siloxanes, vinylmethyl and dimethylpolysiloxane copolymers, vinyl-dimethyl terminated vinylmethyl and dimethylpolysiloxane copolymers, divinylmethyl terminated polydimethylsiloxanes, and vinylphenylmethyl terminated polydimethylsiloxanes. Further, some methyl-modified polysiloxanes that may be used include, but are not limited to, dimethyl-hydro terminated polydimethylsiloxanes, methylhydro and dimethyl-polysiloxane copolymers, methylhydro terminated methyloctyl siloxane copolymers and methylhydro and phenylmethyl siloxane copolymers. In addition, some examples of amino-modified polysiloxanes include, but are not limited to, polymethyl (3-aminopropyl)-siloxane and polymethyl [3-(2-aminoethyl) aminopropyl]-siloxane.

The particular polysiloxanes described above are meant to include hetero- or co-polymers formed from polymerization or copolymer-ization of dimethylsiloxane cyclics and diphenylsiloxane cyclics or trifluoropropylsiloxane cyclics with appropriate endcapping units. Thus, for example, the terms "diphenyl modified dimethylpolysiloxanes" and "copoloymers of diphenylpolysiloxane and dimethylpolysiloxane" may be used interchangeably. Moreover, other examples of polysiloxanes that may be used with the present invention are described in U.S. Pat. No. 5,742,943 to Chen and U.S. Pat. No. 6,306,514 to Weikel, et al., which are incorporated herein in their entirety by reference thereto for all purposes.

In some embodiments, the lubricant layer may include a silicone emulsion. One such silicone emulsion that may be suitable for use with the present invention is DC 365, a pre-emulsified silicone (35% TSC) that is commercially available from Dow Corning Corporation (Midland, Mich.). DC 365 is believed to contain 40–70 mass % water, 30–60 mass % methyl-modified polydimethylsiloxane, 1–5 mass % propylene glycol, 1–5 mass % polyethylene glycol sorbitan monolaurate, and 1–5 mass % octylphenoxy polyethoxy ethanol. Another silicone emulsion that may be suitable for use with the present invention is SM 2140, commercially available from GE Silicones (Waterford, N.Y.). SM 2140 is a pre-emulsified silicone (50% TSC) that is believed to contain 30–60 mass % water, 30–60 mass % amino-modified polydimethyl-siloxane, 1–5% ethoxylated nonyl phenol, 1–5 mass % trimethyl-4-nonyloxypolyethyleneoxy ethanol, and minor percentages of acetalde-hyde, formaldehyde, and 1,4 dioxane. Another silicone emulsion that may be suitable for use with the present invention is SM 2169 available from GE Silicones (Waterford, N.Y.). SM 2169 is a pre-emulsified silicone that is believed to contain 30–60 mass % water, 60–80 mass % polydimethylsiloxane, 1–5 mass % polyoxyethylene lauryl ether, and a small amount of formaldehyde. Yet another silicone that may be suitable for use with the present invention is commercially available from GE Silicones (Waterford, N.Y.) under the trade name AF-60. AF-60 is believed to contain polydimethylsiloxane, acetylaldehyde, and small percentages of emulsifiers. If desired, these pre-emulsified silicones may be diluted with water or other solvents prior to use.

In another embodiment, the lubricant layer may contain a quaternary ammonium compound, such as that commercially available from Goldschmidt Chemical Corporation of Dublin, Ohio under the trade name VERISOFT® BTMS. VERISOFT® BTMS is believed to contain behnyl trimethyl sulfate and cetyl alcohol. Thus for example, in one embodiment, the lubricant layer includes a quaternary ammonium compound such as VERISOFT® BTMS and a silicone emulsion such as SM 2169.

In another embodiment, the lubricant may include, for example, a cationic surfactant (e.g., cetyl pyridinium chloride), an anionic surfactant (e.g., sodium lauryl sulfate), a nonionic surfactant, an amphoteric surfactant, or a combination thereof.

In some embodiments, one or more cationic surfactants may be used. Examples of cationic surfactants that may be suitable for use with the present invention include, for example, behenetrimonium methosulfate, distearyldimonium chloride, dimethyl dioctadecyl ammonium chloride, cetylpyridinium chloride, methylbenzethonium chloride, hexadecylpyridinium chloride, hexadecyltrimethylammonium chloride, benzalkonium chloride, dodecylpyridinium chloride, the corresponding bromides, hydroxyethylheptadecylimidazolium halides, coco aminopropyl betaine, and coconut alkyldimethylammonium betaine. Additional cationic surfactants that may be used include methyl bis (hydrogenated tallow amidoethyl)-2-hydroxyethly ammonium methyl sulfate, methyl bis(tallowamido ethyl)-2-hydroxyethyl ammonium methyl sulfate, methyl bis(soya amidoethyl)-2-hydroxyethyl ammonium methyl sulfate, methyl bis(canola amidoethyl)-2-hydroxyethyl ammonium methyl sulfate, methyl bis(tallowamido ethyl)-2-tallow imidazolinium methyl sulfate, methyl bis(hydrogenated tallowamido ethyl)-2-hydrogenated tallow imidazolinium methyl sulfate, methyl bis(ethyl tallowate)-2-hydroxyethyl ammonium methyl sulfate, methyl bis(ethyl tallowate)-2-hydroxyethyl ammonium methyl sulfate, dihydrogenated tallow dimethyl ammonium chloride, didecyl dimethyl ammonium chloride, dioctyl dimethyl ammonium chloride, octyl decyl dimethyl ammonium chloride diamidoamine ethoxylates, diamidoamine imidazolines, and quaternary ester salts.

In some embodiments, one or more nonionic surfactants may be used. Nonionic surfactants typically have a hydrophobic base, such as a long chain alkyl group or an alkylated aryl group, and a hydrophilic chain comprising a certain number (e.g., 1 to about 30) of ethoxy and/or propoxy moieties. Examples of some classes of nonionic surfactants that may be used include, but are not limited to, ethoxylated alkylphenols, ethoxylated and propoxylated fatty alcohols, polyethylene glycol ethers of methyl glucose, polyethylene glycol ethers of sorbitol, ethylene oxide-propylene oxide block copolymers, ethoxylated esters of fatty ($C_8$–$C_{18}$) acids, condensation products of ethylene oxide with long chain amines or amides, condensation products of ethylene oxide with alcohols, and mixtures thereof.

Specific examples of suitable nonionic surfactants include, but are not limited to, methyl gluceth-10, PEG-20 methyl glucose distearate, PEG-20 methyl glucose sesquistearate, $C_{11-15}$ pareth-20, ceteth-8, ceteth-12, dodoxynol-12, laureth-15, PEG-20 castor oil, polysorbate 20, steareth-20, polyoxyethylene-10 cetyl ether, polyoxyethylene-10 stearyl ether, polyoxyethylene-20 cetyl ether, polyoxyethylene-10 oleyl ether, polyoxyethylene-20 oleyl ether, an ethoxylated nonylphenol, ethoxylated octylphenol, ethoxylated dodecylphenol, or ethoxylated fatty ($C_6$–$C_{22}$) alcohol, including 3 to 20 ethylene oxide moieties, polyoxyethylene-20 isohexadecyl ether, polyoxyethylene-23 glycerol laurate, polyoxy-ethylene-20 glyceryl stearate, PPG-10 methyl glucose ether, PPG-20 methyl glucose ether, polyoxyethylene-20 sorbitan monoesters, polyoxyethylene-80 castor oil, polyoxyethylene-15 tridecyl ether, polyoxyethylene-6 tridecyl ether, laureth-2, laureth-3, laureth-4, PEG-3 castor oil, PEG 600 dioleate, PEG 400 dioleate, oxyethanol, 2,6,8-trimethyl-4-nonyloxypolyethylene oxyethanol; octylphenoxy polyethoxy ethanol, nonylphenoxy polyethoxy ethanol, 2,6,8-trimethyl-4-nonyloxypolyethylene alkyleneoxy-polyethyleneoxyethanol, alkyleneoxypolyethyleneoxyethanol; alkyleneoxypolyethyleneoxyethanol, and mixtures thereof.

Additional nonionic surfactants that may be used include water soluble alcohol ethylene oxide condensates that are the condensation products of a secondary aliphatic alcohol containing between about 8 to about 18 carbon atoms in a straight or branched chain configuration condensed with between about 5 to about 30 moles of ethylene oxide. Such nonionic surfactants are commercially available under the trade name Tergitol® from Union Carbide Corp., Danbury, Conn. Specific examples of such commercially available nonionic surfactants of the foregoing type are $C_{11}$–$C_{15}$ secondary alkanols condensed with either 9 moles of ethylene oxide (Tergitol® 15-S-9) or 12 moles of ethylene oxide (Tergitol® 15-S-12) marketed by Union Carbide Corp., (Danbury, Conn.).

Other suitable nonionic surfactants include the polyethylene oxide condensates of one mole of alkyl phenol containing from about 8 to 18 carbon atoms in a straight- or branched-chain alkyl group with about 5 to 30 moles of ethylene oxide. Specific examples of alkyl phenol ethoxylates include nonyl condensed with about 9.5 moles of ethylene oxide per mole of nonyl phenol, dinonyl phenol condensed with about 12 moles of ethylene oxide per mole of phenol, dinonyl phenol condensed with about 15 moles of ethylene oxide per mole of phenol and diisoctylphenol condensed with about 15 moles of ethylene oxide per mole of phenol. Commercially available nonionic surfactants of this type include Igepal® CO-630 (a nonyl phenol ethoxylate) marketed by ISP Corp. (Wayne, N.J.). Suitable nonionic ethoxylated octyl and nonyl phenols include those having from about 7 to about 13 ethoxy units.

In some embodiments, one or more amphoteric surfactants may be used. One class of amphoteric surfactants that may suitable for use with the present invention includes the derivatives of secondary and tertiary amines having aliphatic radicals that are straight chain or branched, where one of the aliphatic substituents contains from about 8 to 18 carbon atoms and at least one of the aliphatic substituents contains an anionic water-solubilizing group, such as a carboxy, sulfonate, or sulfate group. Some examples of amphoteric surfactants include, but are not limited to, sodium 3-(dodecylamino)propionate, sodium 3-(dodecylamino)-propane-1-sulfonate, sodium 2-(dodecylamino)ethyl sulfate, sodium 2-(dimethylamino)octadecanoate, disodium 3-(N-carboxymethyl-dodecylamino)propane-1-sulfonate, sodium 1-carboxy-methyl-2-undecylimidazole, disodium octadecyliminodiacetate, and sodium N,N-bis(2-hydroxyethyl)-2-sulfato-3-dodecoxypropylamine.

Additional classes of suitable amphoteric surfactants include phosphobetaines and phosphitaines. For instance, some examples of such amphoteric surfactants include, but are not limited to, sodium coconut N-methyl taurate, sodium oleyl N-methyl taurate, sodium tall oil acid N-methyl taurate, cocodimethylcarboxymethylbetaine, lauryl-dimethylcarboxymethylbetaine, lauryldimethylcarboxyethylbetaine, cetyldimethylcarboxymethylbetaine, sodium palmitoyl N-methyl taurate, oleyldimethylgammacarboxypropylbetaine, lauryl-bis-(2-hydroxypropyl)-carboxyethylbetaine, di-sodium oleamide PEG-2 sulfosuccinate, laurylamido-bis-(2-hydroxyethyl) propylsultaine, lauryl-bis-(2-hydroxy-ethyl) carboxymethylbetaine, cocoamidodimethylpropylsultaine, stearylamidodimethylpropylsultaine, TEA oleamido PEG-2 sulfosuccinate, disodium oleamide MEA sulfosuccinate, disodium oleamide MIPA sulfosuccinate, disodium ricinoleamide MEA sulfosuccinate, disodium undecylenamide MEA sulfosuccinate, disodium wheat germamido MEA sulfosuccinate, disodium wheat germamido PEG-2 sulfosuccinate, disodium isostearamideo MEA sulfosuccinate, cocoamido propyl monosodium phosphitaine, lauric myristic amido propyl monosodium phosphitaine, cocoamido disodium 3-hydroxypropyl phosphobetaine, lauric myristic amido disodium 3-hydroxypropyl phosphobetaine, lauric myristic amido glyceryl phosphobetaine, lauric myristic amido carboxy disodium 3-hydroxypropyl phosphobetaine, cocoamphoglycinate, cocoampho-carboxyglycinate, capryloamphocarboxyglycinate, lauroamphocarboxy-glycinate, lauroamphoglycinate, capryloamphocarboxypropionate, lauro-amphocarboxypropionate, cocoamphopropionate, cocoamphocarboxy-propionate, dihydroxyethyl tallow glycinate, and mixtures thereof.

In certain instances, one or more anionic surfactants may be used. Suitable anionic surfactants include, but are not limited to, alkyl sulfates, alkyl ether sulfates, alkyl ether sulfonates, sulfate esters of an alkylphenoxy polyoxyethylene ethanol, alpha-olefin sulfonates, beta-alkoxy alkane sulfonates, alkylauryl sulfonates, alkyl monoglyceride sulfates, alkyl monoglyceride sulfonates, alkyl carbonates, alkyl ether carboxylates, fatty acids, sulfosuccinates, sarcosinates, octoxynol or nonoxynol phosphates, taurates, fatty taurides, fatty acid amide polyoxyethylene sulfates, isethionates, or mixtures thereof.

Particular examples of some suitable anionic surfactants include, but are not limited to, $C_8$–$C_{18}$ alkyl sulfates, $C_8$–$C_{18}$ fatty acid salts, $C_8$–$C_{18}$ alkyl ether sulfates having one or two moles of ethoxylation, $C_8$–$C_{18}$ alkamine oxides, $C_8$–$C_{18}$ alkoyl sarcosinates, $C_8$–$C_{18}$ sulfoacetates, $C_8$–$C_{18}$ sulfosuccinates, $C_8$–$C_{18}$ alkyl diphenyl oxide disulfonates, $C_8$–$C_{18}$ alkyl carbonates, $C_8$–$C_{18}$ alpha-olefin sulfonates, methyl ester sulfonates, and blends thereof. The $C_8$–$C_{18}$ alkyl group may be straight chain (e.g., lauryl) or branched (e.g., 2-ethylhexyl). The cation of the anionic surfactant may be an alkali metal (e.g., sodium or potassium), ammonium, $C_1$–$C_4$ alkylammonium (e.g., mono-, di-, tri), or $C_1$–$C_3$ alkanolammonium (e.g., mono-, di-, tri).

Specific examples of such anionic surfactants include, but are not limited to, lauryl sulfates, octyl sulfates, 2-ethylhexyl sulfates, lauramine oxide, decyl sulfates, tridecyl sulfates, cocoates, lauroyl sarcosinates, lauryl sulfosuccinates, linear $C_{10}$ diphenyl oxide disulfonates, lauryl sulfosuccinates, lauryl ether sulfates (1 and 2 moles ethylene oxide), myristyl sulfates, oleates, stearates, tallates, ricinoleates, cetyl sulfates, and so forth.

The article of the present invention features enhanced donning characteristics. The presence of covalently bonded porous beads within the article decreases the overall coefficient of friction of the surface, permits the glove to be donned more readily, and enables the application of a desirable treatment to be imparted to the end user wearing or otherwise contacting the article. Further, since the particles are chemically covalently bonded the article, no additional binder is needed. This provides a processing advantage over other particulate compositions that require use of a binder to ensure that particles will not inadvertently dissociate from the glove. Additionally, where a lubricant is utilized in accordance with the present invention, donning is further enhanced.

The invention may be embodied in other specific forms without departing from the scope and spirit of the inventive characteristics thereof. The present embodiments therefore are to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. An elastomeric article comprising: a substrate body including a hydrocarbon-based elastomeric polymeric matrix; a plurality of porous beads having a pore size that ranges from about 0.01 microns to about 0.5 microns, the beads containing a treatment impregnated within said pores, the treatment being time-releasable to an environment; and each of said beads has a surface with at least a vinyl functional group, and said bead is covalently bonded to said elastomeric polymer matrix or a coating thereon.

2. The article according to claim 1, wherein said vinyl group is selected from the group consisting of a carbon-carbon vinyl group and an acrylate group.

3. The article according to claim 1, wherein said porous bead has a porosity of about 0.1% to about 90% of the entire volume of said bead.

4. The article according to claim 3, wherein said porous bead has a porosity of about 20% to about 90% of the entire volume of said bead.

5. The article according to claim 1, wherein said porous beads are present in an amount of from about 0.0001 mass % to about 10 mass % of said article.

6. The article according to claim 1, wherein said porous beads do not plasticize, dissolve, dissociate, or degrade during formation of said article.

7. The ankle according to claim 1, wherein said porous beads are formed from a material that either has or does not have hydrocyl functionality, but can be surface converted to produce hydroxyl groups on a surface of said beads.

8. The article according to claim 1, wherein either a diffusion mechanism or a shearing force mechanism is employed to control timed-release of said treatment.

9. The article according to claim 1, wherein said treatment includes a moisturizer, an ointment, a drug, or an emollient.

10. The article according to claim 1, wherein said treatment enhances skin-health.

11. The article according to claim 10, wherein said treatement is selected from the group consisting of aloe, vitamin E, lanolin, polyethylene glycol, glycerin, and mineral oil.

12. The article according to claim 1, wherein said environment comprises an end user's skin.

13. The article according to claim 1, wherein said coating on said elastomer polymer matrix comprises a donning layer.

14. The article according to claim 1, wherein said porous beads are present in an amount of about 0.01 mass % to about 80 mass % of said donning layer.

15. The article according to claim 1, wherein said porous beads are present on an inside surface.

16. An elastomeric article comprising: an elastomeric substrate body having a first surface; and a donning layer overlying said first surface, the donning layer comprising a polymer material containing a plurality of porous beads with a surface having reactive vinyl functional groups, said beads are covalently bonded to either said substrate body or said donning layer by means of a C—C bond.

17. The elastomeric article according to claim 16, where said beads contain a time-releasable treatment in a number of pores.

18. The elastomeric article according to claim 16, wherein said polymer material comprises a hydrogel.

19. The elastomeric article according to claim 16, wherein said elastomeric substrate body has a second surface distal from said donning layer, and said second surface contains a plurality of porous beads covalently attached to said second surface.

20. The article according to claim 16, wherein said article is either a glove or a condom.

* * * * *